(12) United States Patent
Nino et al.

(10) Patent No.: US 9,943,948 B2
(45) Date of Patent: *Apr. 17, 2018

(54) FORTIFIED PLASTIC DISPOSABLE TORQUE DEVICES

(71) Applicant: ECA Medical Instruments, Newbury Park, CA (US)

(72) Inventors: John Nino, Simi Valley, CA (US); David Ivinson, Camarillo, CA (US)

(73) Assignee: ECA MEDICAL INSTRUMENTS, Newbury Park, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 14/806,144

(22) Filed: Jul. 22, 2015

(65) Prior Publication Data
US 2015/0321327 A1  Nov. 12, 2015

Related U.S. Application Data

(63) Continuation of application No. PCT/US2014/010907, filed on Jan. 9, 2014.
(Continued)

(51) Int. Cl.
*B25B 23/14* (2006.01)
*A61B 17/88* (2006.01)
(Continued)

(52) U.S. Cl.
CPC ...... *B25B 23/1415* (2013.01); *A61B 17/8875* (2013.01); *A61B 90/03* (2016.02);
(Continued)

(58) Field of Classification Search
CPC ............ B25B 23/1415; B25B 23/1427; B25B 23/141; B25B 15/04; B25B 23/0042;
(Continued)

(56) References Cited

U.S. PATENT DOCUMENTS 6,132,435 A  10/2000  Young
7,197,968 B2  4/2007  Bubel
(Continued)

FOREIGN PATENT DOCUMENTS

WO  WO 2003/013372 A2  2/2003
WO  WO 2005/077603 A1  8/2005
(Continued)

OTHER PUBLICATIONS

International Patent Application No. PCT/US2014/010907; Int'l Preliminary Report on Patentability; dated Aug. 6, 2015; 12 pages.
(Continued)

*Primary Examiner* — Robert Scruggs
(74) *Attorney, Agent, or Firm* — Baker & Hostetler LLP

(57) ABSTRACT

A fortified plastic disposable driver having a plastic generally conical nose with a top and bottom, the bottom formed as part of or affixed to the flat top of a body and the top of the nose having a square channel guide with corners, is disclosed. The channel accepts a tool or shaft. At 90 degree orientation from each other are four pairs of force buttressing ribs wherein they have a bottom affixed at said flat top, and each has a support edge affixed to an annular outer wall of the nose. The four pairs of ribs, each pair being positioned along one of the four sides of the square channel. In some instances, each rib further comprises an interior edge and an outer edge, and each outer edge is aligned with a corner. A body and/or handle are used therewith to impart torque for use.

15 Claims, 11 Drawing Sheets

Related U.S. Application Data

(60) Provisional application No. 61/755,823, filed on Jan. 23, 2013.

(51) Int. Cl.
    *B25B 15/04*     (2006.01)
    *B25B 23/142*     (2006.01)
    *A61B 90/00*     (2016.01)
    *B25B 23/00*     (2006.01)

(52) U.S. Cl.
    CPC .......... *B25B 15/04* (2013.01); *B25B 23/0042* (2013.01); *B25B 23/141* (2013.01); *B25B 23/1427* (2013.01); *A61B 2090/031* (2016.02)

(58) Field of Classification Search
    CPC .......... A61B 17/8875; A61B 2090/031; A61B 2090/037; A61B 90/03
    See application file for complete search history.

(56) References Cited

U.S. PATENT DOCUMENTS

| | | |
|---|---|---|
| 7,243,581 B1 | 7/2007 | Gao |
| 2006/0254392 A1 | 11/2006 | Frank |
| 2012/0198972 A1* | 8/2012 | Nino .................... B25B 15/04 81/471 |

FOREIGN PATENT DOCUMENTS

| | | |
|---|---|---|
| WO | WO 2012/112591 A2 | 8/2012 |
| WO | WO 2012/112812 A2 | 8/2012 |

OTHER PUBLICATIONS

European Patent Application No. 14743425.2; Search Report; dated Mar. 2, 2017; 9 pages.

* cited by examiner

FORTIFIED PLASTIC DISPOSABLE TORQUE DEVICES

CROSS REFERENCE TO RELATED APPLICATIONS

This Utility patent application is a Continuation of International patent application PCT/US2014/010907 filed Jan. 9, 2014, which claims the full Paris Convention benefit of and priority to U.S. provisional application No. 61/755,823 filed Jan. 23, 2013, the contents of which are incorporated by this reference as if fully set forth herein in their entirety.

BACKGROUND

1. Field

This disclosure relates to a plastic disposable driver fortified to withstand higher forces.

2. General Background

Torque drivers and torque limiting drivers are widely used throughout manufacturing, assembly and the medical industry. Torque-limiting drivers have a factory pre-set torque to ensure the accuracy and toughness required to meet a demanding surgical environment. Disposable torque drivers are often rated to withstand a maximum rotational force applied thereto before the mounting of a drive tool fails.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task, but must be done routinely.

Disposable drivers are an easy to use and reliable alternative to the reusable drivers. Typically, a medical device such as an implant, for example, is packaged with a disposable driver designed to the implant's specifications. Once the driver has been used, it can be discarded. Thus, a surgeon can have complete confidence that the disposable driver, packaged with an implant, will impart either the precise amount of torque required or at least the amount of torque required (for fixed devices). Typically, the torque requirement is different for different operations and for different implants. For example, applications may include those in the field of orthopedic surgery, construction and emplacement of implants, etc.

These disposable drivers have been used for low torque applications. The standard torque values in these applications typically range from 4 to 20 inch-ounces. It has, however, been a challenge to develop a reliable disposable driver capable of imparting higher torques for larger applications.

DISCLOSURE

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N m). The joule, which is the SI unit for energy or work, is also defined as an Nm, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A fortified plastic connector mount, in accordance with the present disclosure, has a handle, a body, and a workpiece engaging tip. Within the cylindrical body there is a torque-limiting assembly. The torque-limiting assembly includes an upper cylindrical shank and a lower cylindrical shank. The upper cylindrical shank and the lower cylindrical shank have a plurality of teeth. The teeth have a vertical face, an inclined face, and a substantially flat peak. The inclined face is defined by a first radius of curvature that transitions to the substantially flat peak. The teeth are spaced circumferentially and spiral around the upper cylindrical shank and a lower cylindrical shank. There is a spring for applying pressure across the upper cylindrical shank and the lower cylindrical shank. The teeth of the upper cylindrical shank and the lower cylindrical shank engage for relative rotation when the handle is turned, and disengage when a predetermined value of torque is exceeded.

A fortified plastic connector mount, in accordance with the present disclosure of a device with a plastic nose having a distal and a proximal end, formed as part of or affixed to the flat top of a body; the nose having a polygonal channel guide with corners. The channel formed axial and centered in the nose and of a size to accept a tool or shaft; at least one pair of force buttressing ribs "FBR" wherein said FBR have a bottom affixed at the flat top and the FBR has a support edge affixed to an annular outer wall of the nose; and, wherein the proximal end of the nose is affixed at the flat top. In some instances the channel is square.

A fortified plastic connector mount, in accordance with the present disclosure of a device with a plastic nose having a distal and a proximal end, formed as part of or affixed to the flat top of a body; the nose having a square channel guide with corners. The channel formed axial and centered in the nose and of a size to accept a tool or shaft; four pairs of force buttressing ribs "FBR" wherein said FBR have a bottom affixed at the flat top and the FBR has a support edge affixed to an annular outer wall of the nose; and, wherein the proximal end of the nose is affixed at the flat top. The four pairs of FBR each pair being positioned along one of the four side of the square channel. In some instances, each FBR further comprises an interior edge and an outer edge and each outer edge is aligned with a corner.

A fortified plastic connector mount, in accordance with the present disclosure of a device with an elongated nose with a distal end fluidly connected to an interior channel formed axially therein; a wall with a predetermined thickness surrounding the interior channel with an outer annular surface; a flat top affixed to or formed as part of the proximal end of the nose; and, at least one pair of force buttressing ribs "FBR" (120 & 120') affixed to both the flat top and the annular wall.

A fortified plastic connector mount, in accordance with the present disclosure of a device with an elongated nose with a distal end fluidly connected to a square interior channel, with four corners, formed axially therein; a wall with a predetermined thickness surrounding the interior channel with an outer annular surface; a flat top affixed to or formed as part of the proximal end of the nose; four pairs of force buttressing ribs "FBR" affixed to both the flat top and the annular wall; and, the four pairs of FBR each aligned with one of the four walls of the interior channel.

According to aspects of exemplary implementations of the present disclosure there is a method of applying torque to a shaft with a plastic disposable driver, the method comprising: applying torque to a drive shaft and the shaft being affixed to a handle via a polygonal channel in a connector mount; an annular wall is formed around the connector mount defining a channel; the channel is part of a larger connector mount that is fortified with at least two pairs of force buttressing ribs "FBR," whereby load from the shaft excreting force on the annular wall is transferred to a flat top of the connector mount; and, whereby the connector mount holds the shaft without failure at a load between a force of 85 and 115 lbf for a predetermined time. In some instances, the polygonal channel is a square with four sides; and, has four pairs of FBRs one pair on each side. In some instance a non-fortified mount will at least one of distort, deform, and break the wall ("W") of the nose ("N") during the predetermined time in the absence of the strategically placed FBRs when the force (F1) is applied.

According to aspects of exemplary implementations of the present disclosure there is a method of applying torque to a shaft with a plastic disposable driver, the method comprising: applying torque to a drive shaft and the shaft being affixed to a handle via a polygonal channel in a connector mount; an annular wall is formed around the connector mount defining a channel; the channel is part of a larger connector mount that is fortified with at least two pairs of force buttressing ribs "FBR" whereby load from the shaft excreting force on the annular wall is transferred to a flat top of the connector mount; and, whereby the connector mount holds the shaft without failure at a load between a force of 85 and 115 lbf for a predetermined time. In some instances the polygonal channel is a square with four sides; and, has four pairs of FBRs one pair on each side In some instance a non-fortified mount will at least one of distort, deform, and break the wall ("W") of the nose ("N") during the predetermined time in the absence of the strategically placed FBRs when the force (F1) is applied. In some instances, each FBR is aligned with a corner. In some instances, the predetermined time is one of at least about 8 seconds, 9 seconds, 10 seconds, 11 seconds and 12 seconds.

According to aspects of exemplary implementations of the present disclosure, there is a method of applying torque to a shaft with a plastic disposable driver, the method comprising: applying torque to a drive shaft and the shaft being affixed to a handle via a polygonal channel in a connector mount; an annular wall is formed around the connector mount defining a channel; the channel is part of a larger connector mount that is fortified with at least two pairs of force buttressing ribs "FBR" whereby load from the shaft excreting force on the annular wall is transferred to a flat top of the connector mount; and, whereby the connector mount holds the shaft without failure at a load between a force of 85 and 115 lbf for a predetermined time. In some instances, the polygonal channel is a square with four sides; and, has four pairs of FBRs, one pair on each side. In some instances, a non-fortified mount will at least one of distort, deform, and break the wall ("W") of the nose ("N") during the predetermined time in the absence of the strategically placed FBRs when the force (F1) is applied. the connection mount holds the shaft without failure at a load between a force (F1) of 140 and 150 pound-feet for at least one of at least about 8 seconds, 9 seconds, 10 seconds, 11 seconds 12 seconds, 13 seconds, 14 seconds, 15 seconds, 16 seconds 17 seconds and 18 seconds.

DRAWINGS

The above-mentioned features of the present disclosure will become more apparent with reference to the following description taken in conjunction with the accompanying drawings wherein like reference numerals denote like elements and in which.

Figure 1:
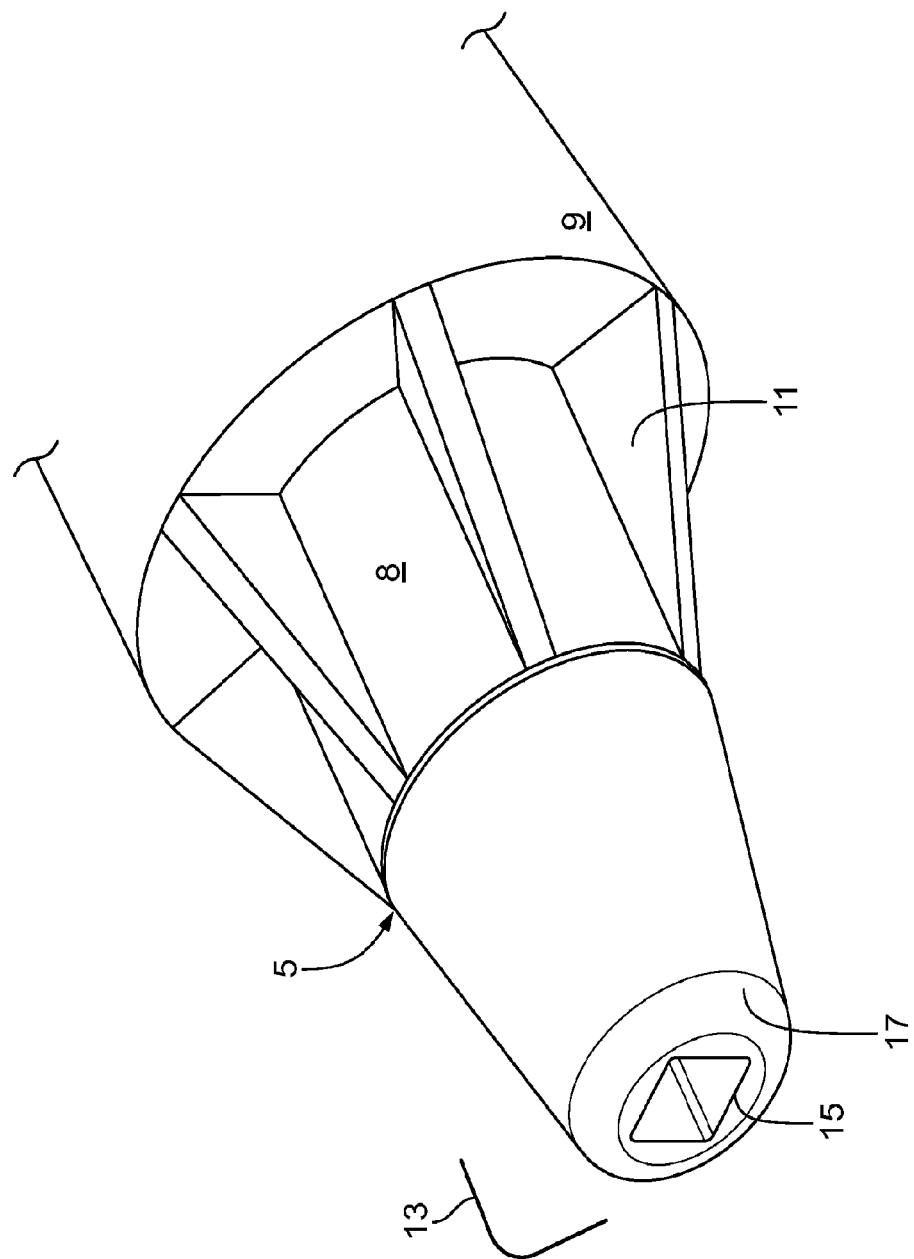
FIG. 1 is a perspective view of a traditional connector mount.
Figure 2:
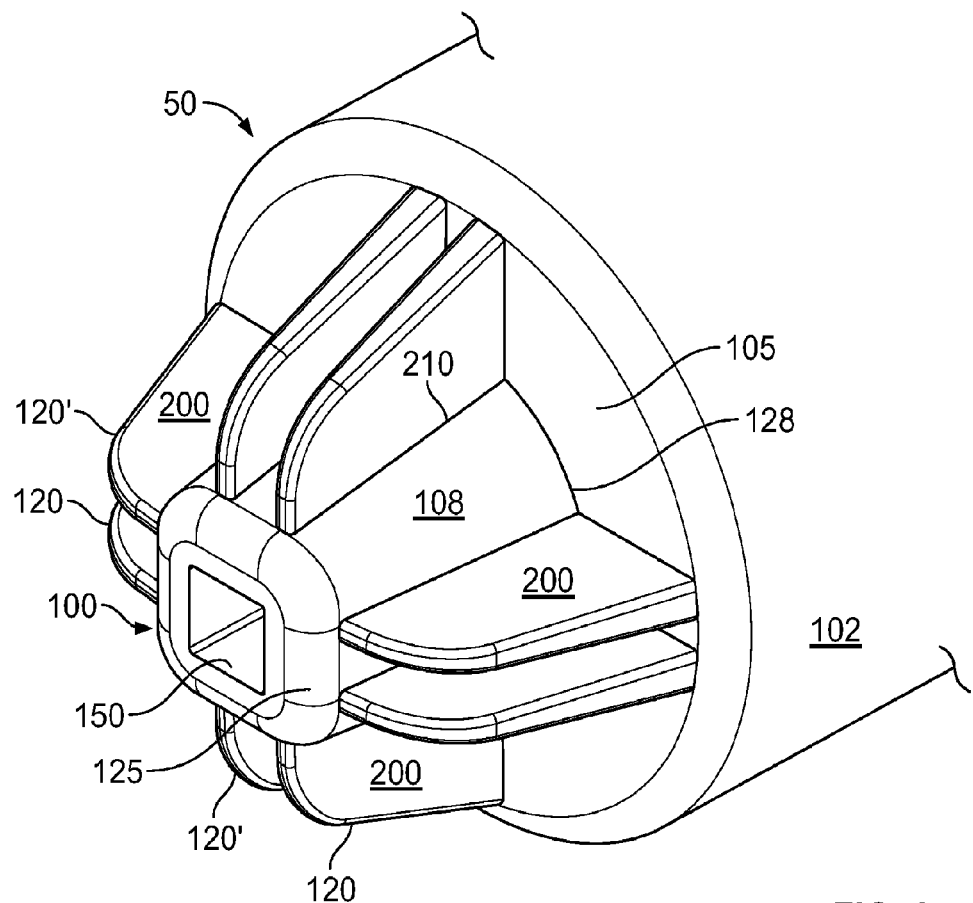
FIG. 2 is a perspective view of a fortified connector mount in accordance with the present disclosure.
Figure 3:
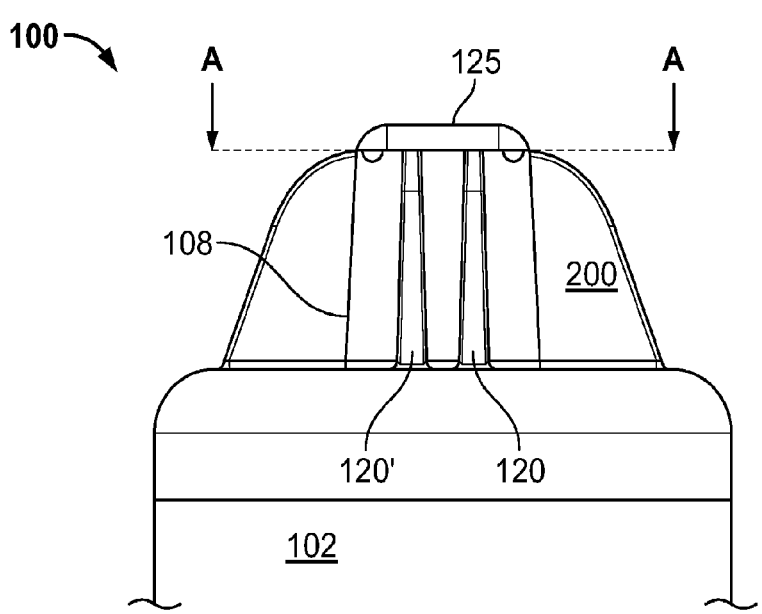
FIG. 3 is a side view of a fortified connector mount in accordance with the present disclosure.
Figure 4:
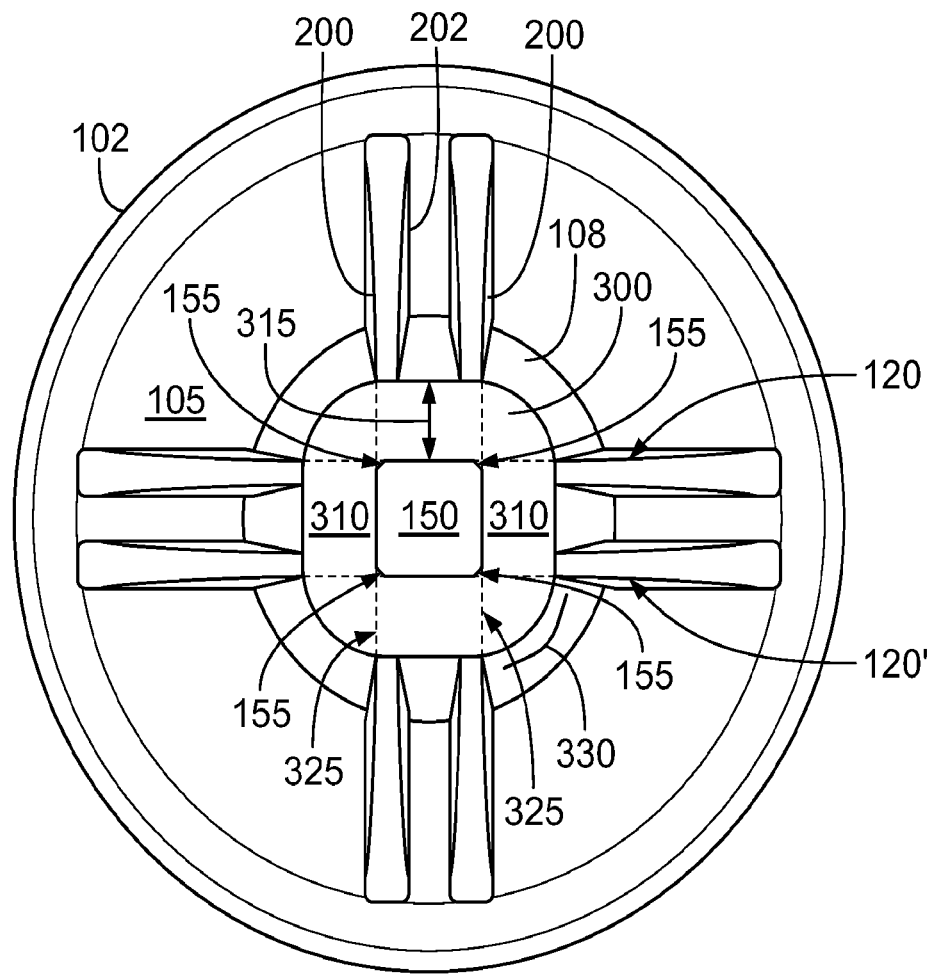
FIG. 4 is a cut away along line "A-A" top perspective view of a fortified connector mount in accordance with the present disclosure.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DISCLOSURE

Figure 6:
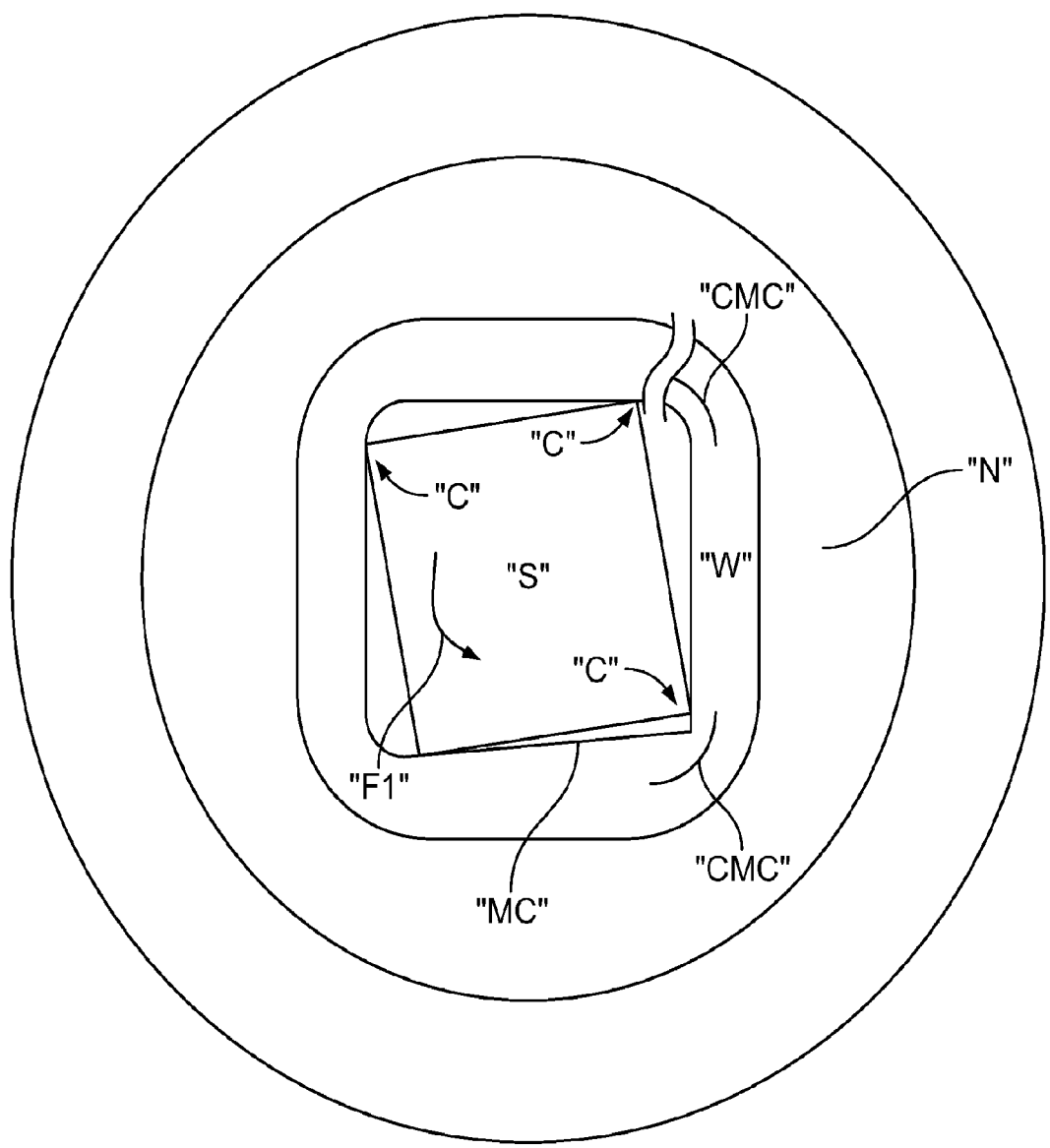
FIG. 6 is a diagrammatic view of how a traditional non-fortified connector mount will fail fails under the same force the fortified mount of FIG. 5 will tolerate.
Figure 7:
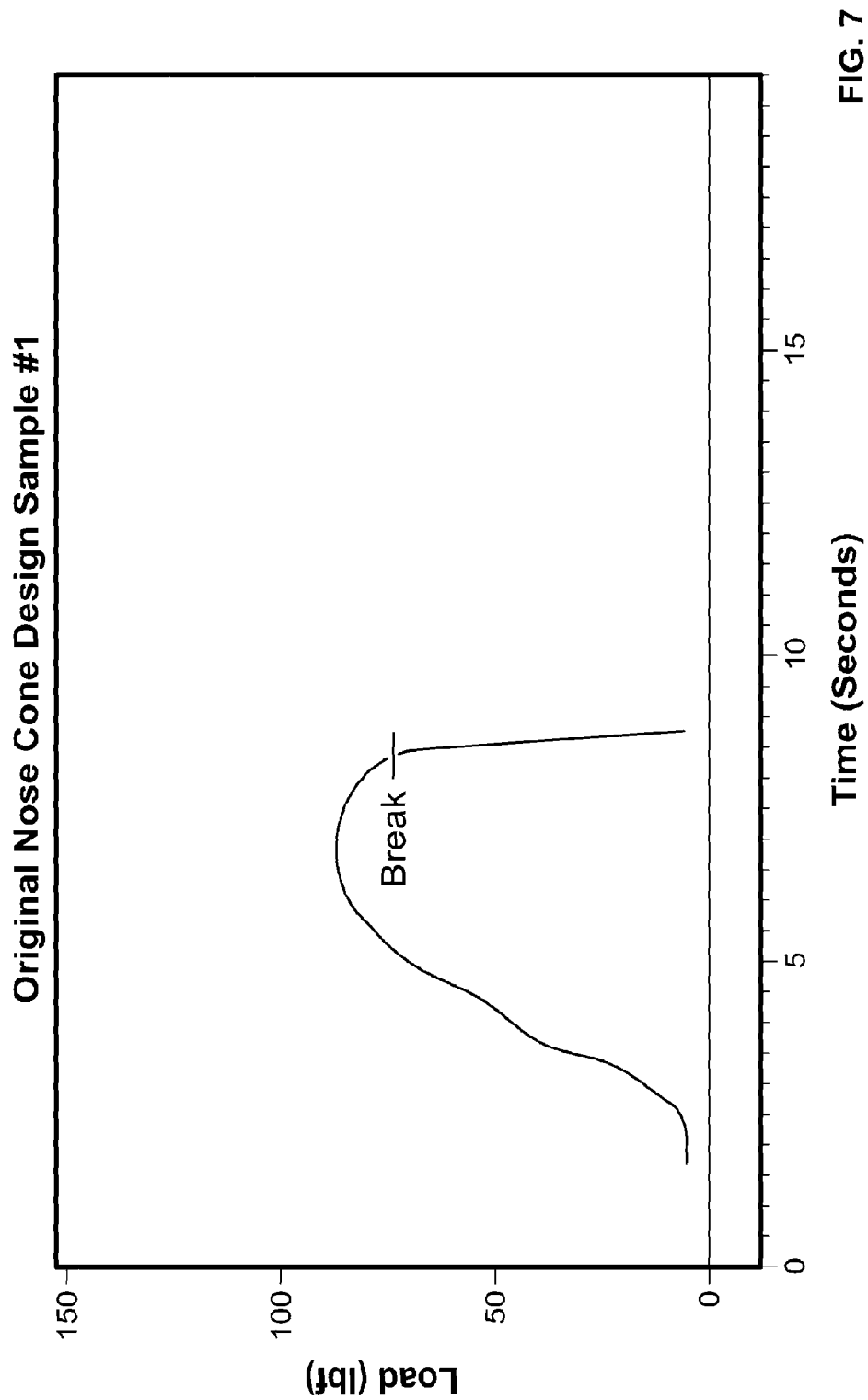
FIGS. 7 and 8 are charts showing test to failure for a traditional mount shown in FIG. 1.
Figure 8:
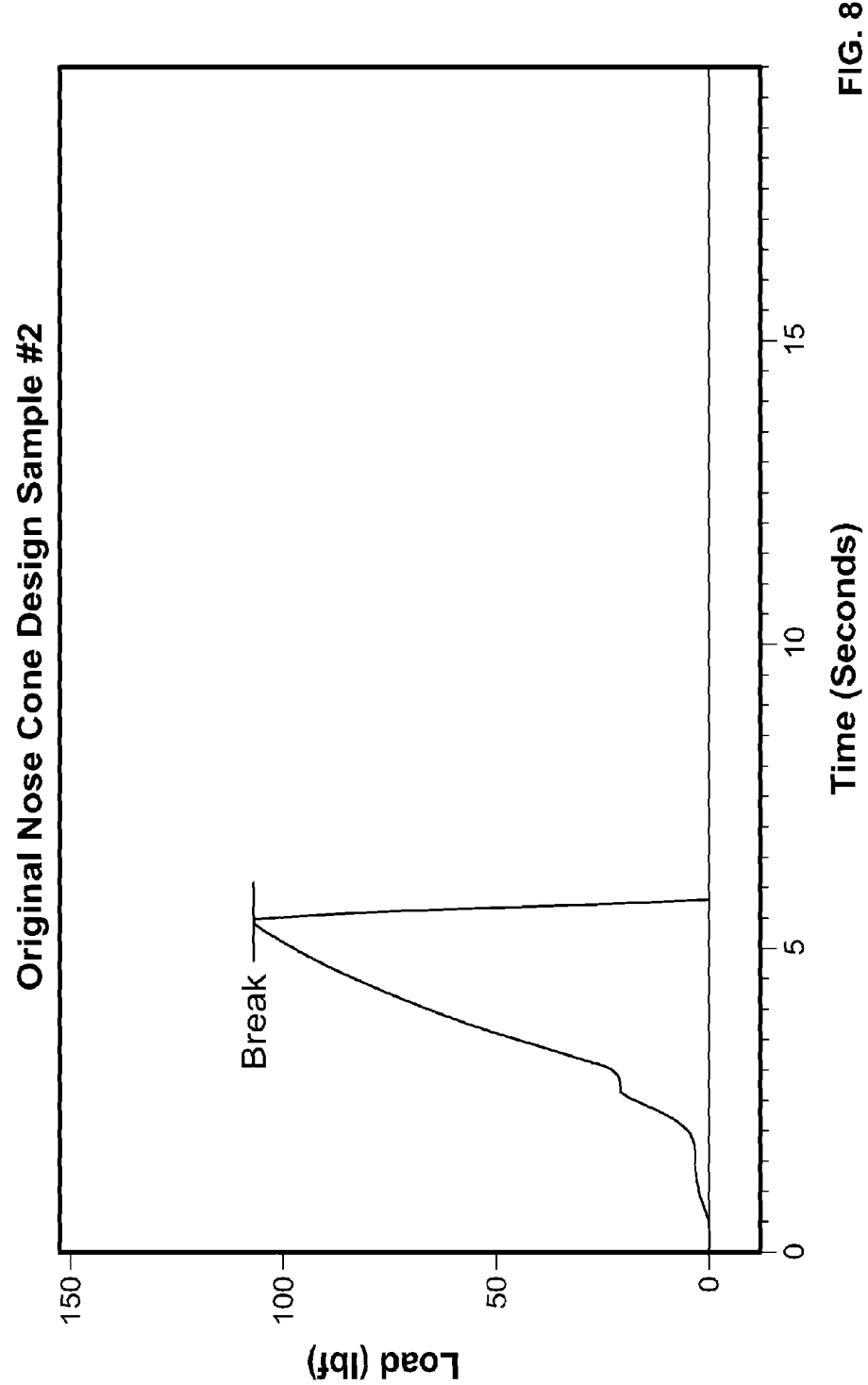

Referring to FIGS. 1, 6, 7 and 8, there is a plastic molded connection mount 5 representative of traditional strength molded mounts for fixing or connecting tools and/or other connectors thereto. The connection mount has a nose 7, a neck 8, and are affixed to body 9. Such mounts are used to provide support for a shaft (not shown) and hold fast a shaft against a force applied via rotation of the nose 7 and body 9. A plurality of support flanges 11 are positioned around a neck 8 to add strength while saving material. A connection mount has at its distal end 13 a guide 15 whereby a tool or shaft (not shown) may be mounted. An annular wall 17 surrounds the connection mount. FIGS. 7 and 8 are findings from two tests to failures of the performance of the traditional molded mount illustrated in FIG. 1.

Referring to FIGS. 2-5, 9 and 10 there is a plastic molded fortified connector mount "CM" 50. The connector mount is a guide and/or anchor to mount, fix or connect tools and/or other connectors to the CM. The CM mount has a generally conical nose 100, affixed to a body 102. The affixation of nose to body includes molding as a single piece. The body 102 is generally cylindrical and has a flat top 105. The nose 100 has an annular outer wall 108.

A CM supports or encases a shaft (not shown) and holds fast a shaft against a force applied via rotation of the nose 100 and body 102. Even numbered sets of force buttressing ribs (FBR) 120 & 120' are positioned around the outer annular wall 108 of nose 100. At the distal end 125 of the CM is a channel 150, which acts as a guide whereby a tool or shaft may be mounted.

Figure 5:
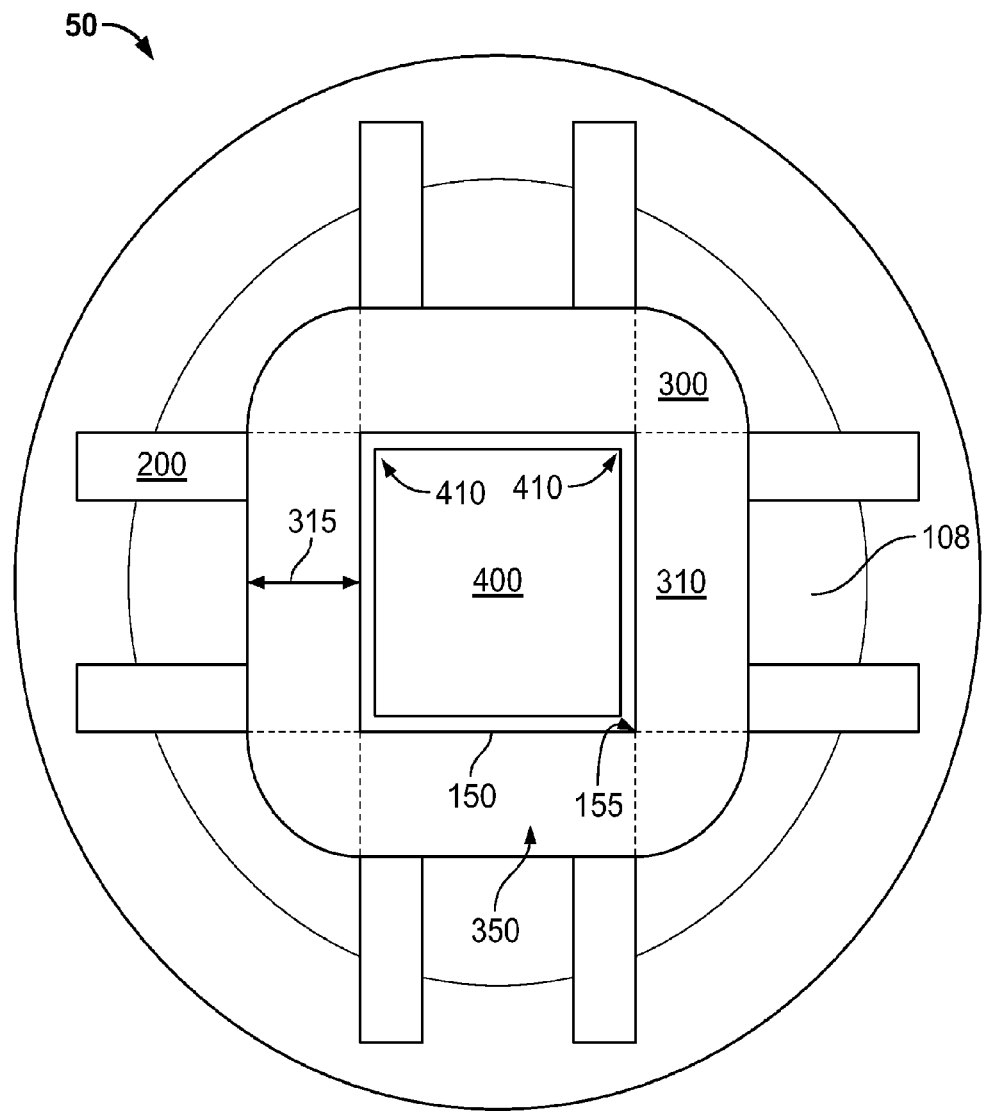
FIG. 5 is a diagrammatic view a fortified connector mount, less susceptible to failure then a traditional mount.

FIG. 5 is a diagrammatic view of the nose in a fortified mount device. When shaft 400 within the drive channel 150, the corners of the shaft 410 are adjacent to the corner channels 155. The drive channel 150 is substantially square. Each channel corner 155 is a region where a plastic mounting will tend to deform, break or otherwise fail under rotational forces. The corners 410 of the shaft when rotated against the channel corners 155 have significant impact on the corners and the plastic nose 100. When shaft 400 within said drive channel 150 is rotated at force one (F1) which is at the maximum tolerance of the fortified connector mount 50, the FBRs support the connection mount and prevent the wall structure, especially at the corners 155 of the nose 350 from distorting or breaking due to failure under F1.

In the unfortified nose as illustrated in FIG. 6 failure will occur as follows. When a shaft "S" within said a mount channel "MC" is rotated at a force which is within the operational tolerance of the disclosed fortified connector mount in FIG. 5 the similar sized non-fortified mount will distort, deform and/or break the wall "W" of the nose "N" in the absence of the strategically placed FBRs when force one (F1) is applied. The corners "C" of the shaft "S" when rotated against the corner of the mounting channel "CMC" have the most significant impact of force upon the nose. It is at those locations of the nose opening where there is the greatest possibility of an unreinforced nose wall to crack. The crack can occur because the opposite side of the wall at the corners does not have any bracing. Moreover, a thicker wall "W" would not make the wall any stronger or less likely to crack, but may in fact make it weaker. When enough force is applied to the opening of the nose cone, the walls of the nose cone can deflect. If the nose cone wall deflects enough, a crack can occur.

In the disclosed fortified mounting the nose 100 is fortified or buttressed against shearing and other forces via very specifically placed ribs 120 & 120'. The wall structure 350 of the nose between the annular outer wall 108 and the channel 150 is separated into alternating zones. Each zone is separated by a fortification. Zone 1 is the corner zone 300, zone 2 is the boundary wall zone 310 and the fortifications 325 are areas of the plastic molded nose 100 which are located substantially directly between each channel corner 155, the annular wall 108 and the outer edge 200 of each rib Boundary wall zone 310 is substantially the same thickness 315 from drive channel 150 to the annular wall 108. That thickness will vary as one moves from the distal end 125 of the nose toward the flat top 105. However, the thickness of boundary wall 310 is substantially the same cross section between fortifications 325. The nose 100 has a proximal end 128 which is affixed to, formed as part of or mounted to the flat top 105 of the body. In some instances the distal end of the nose 125 is generally squareish with rounded or radiused corners 330 in cross section, and the proximal end is generally circular in cross section. In other instances both the distal end of the nose 125 and the proximal end 128 may be generally squareish with rounded or radiuses corners in cross section. In the wall structure 350 the force buttressing ribs (FBR) 120 & 120' are pairs have a bottom edge 201 which is affixed to, or formed as part of or mounted to the flat top 105 of the body and also have interior edges 202 and outer edges 200. The FBR is attached, affixed, or formed as part of the nose 100 on the annular wall 108 of the nose at the FBR support edge (210).

FBRs are positioned to be aligned with an edge or side of the drive channel 150 opening, as well as each corner 155. The FBR brace each corner whether the shaft 400 is being rotated clockwise or counter-clockwise. Ergo, the FBR is preferably in-line with each side of each corner. These FBRs are at 90-degrees apart due to being at 180-degrees to the side of each opening they support. Being at 90-degrees and 180-degrees ensures that each side wall zone 310 and each corner zone 300 is equally braced.

FBRs may be positioned at angles other than 90-degrees or 180-degrees, however, there will be an unbalanced situation where one side could be weaker than the other side, and therefore not reinforcing the adjacent zone adequately to withstand the highest force requirement. Such other angles may be acceptable in lower force situation and are within the scope of this disclosure for such situations. A plastic nose material will eventually crack if force beyond the limits of the use intended is applied. By placing each FRB at a 90-degree angle from its base, the 90-degree angle achieves a balance force load, so that each side of rib receives equal force and therefore eliminates the unbalance.

Figure 9:
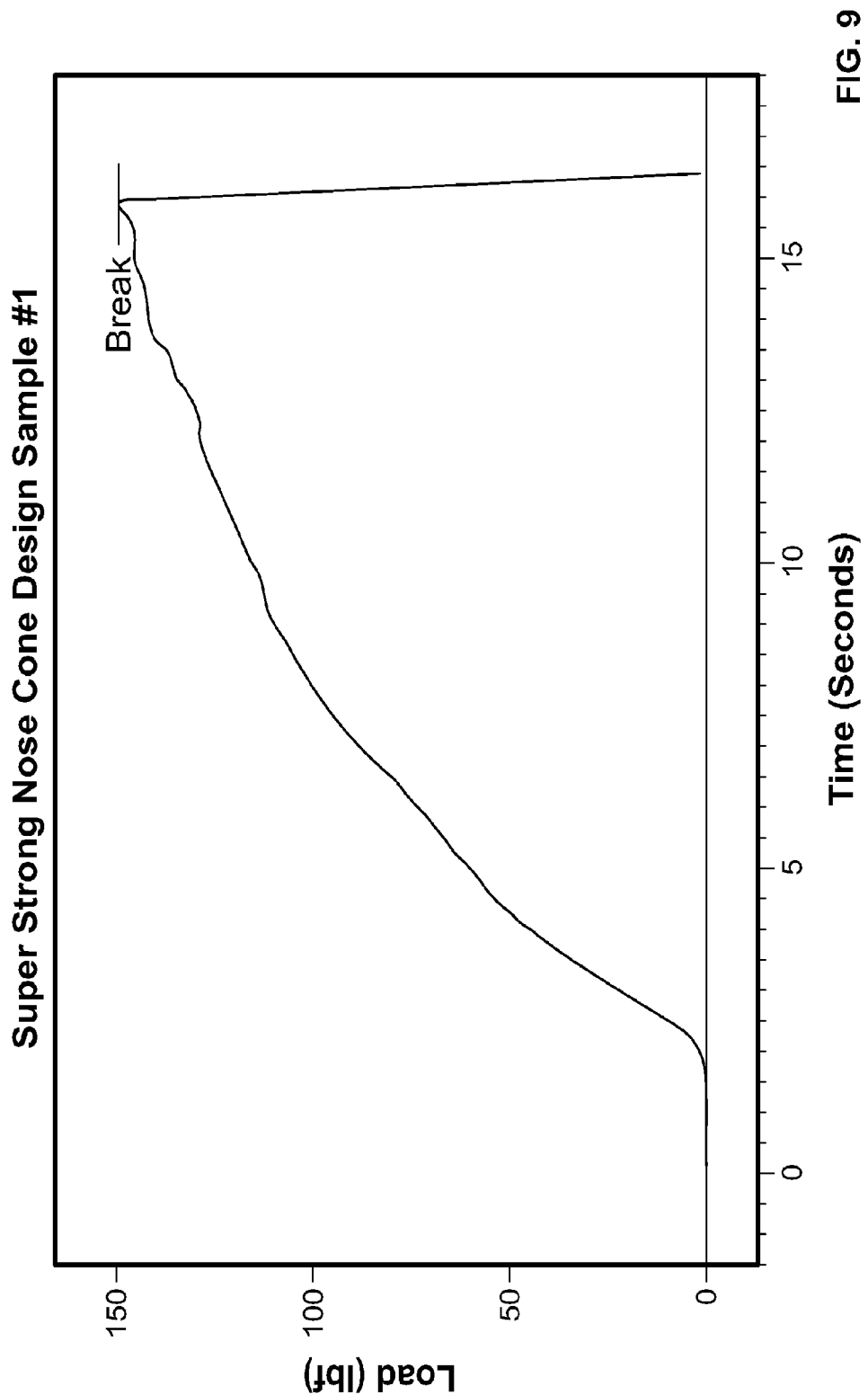
FIGS. 9 and 10 are charts showing test to failure of the fortified mount of FIGS. 2-4.
Figure 10:
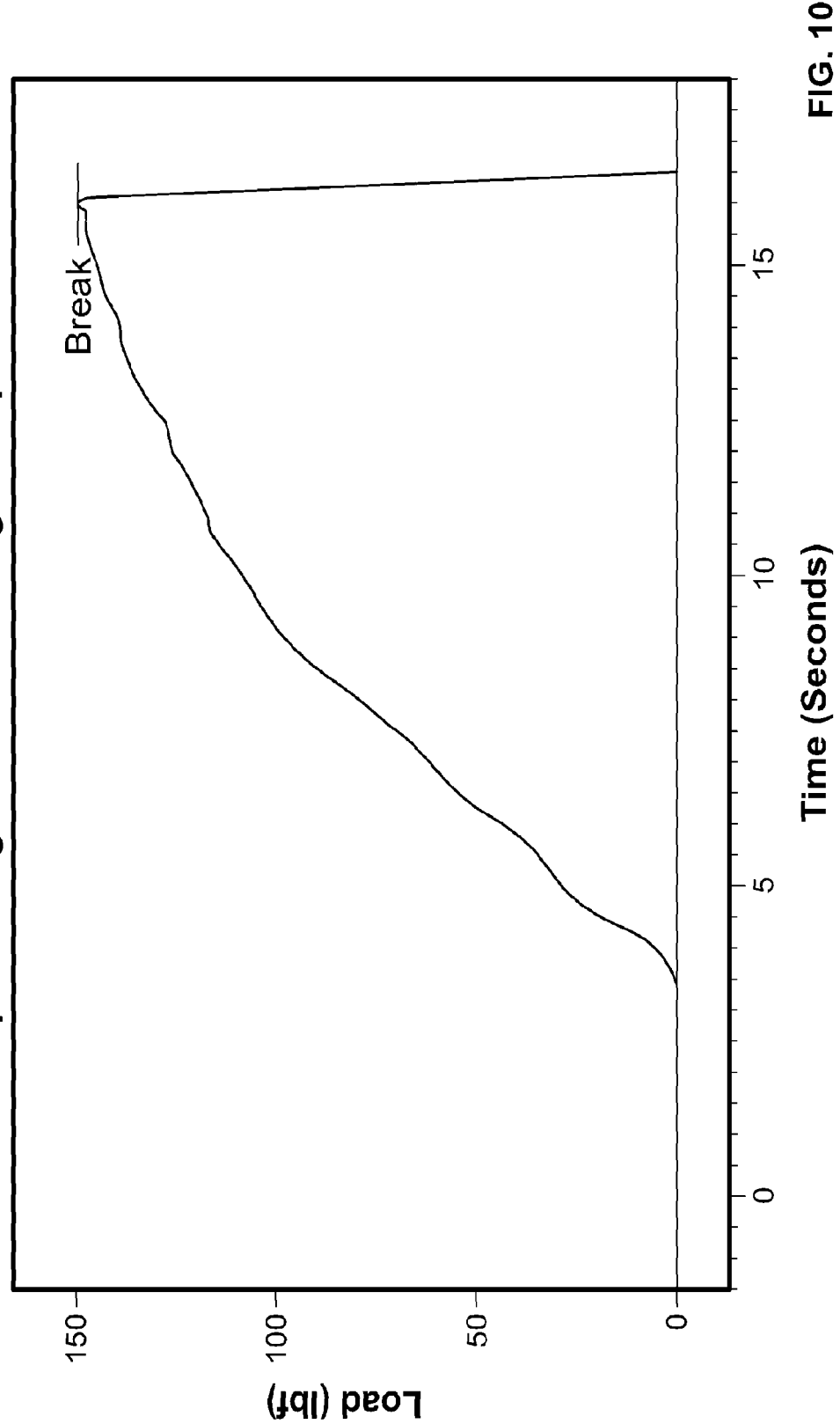

FIGS. 7 and 8 are measurements of a non-fortified connector mount tested to failure. Failure occurs at a load between 115 and 85 lbf and between 7 and 8 seconds. FIGS. 9 and 10 are measurements of a fortified connector mount tested to failure. Failure occurs at a load between 140 and 150 lbf and between 17 and 18 seconds.

Figure 11:
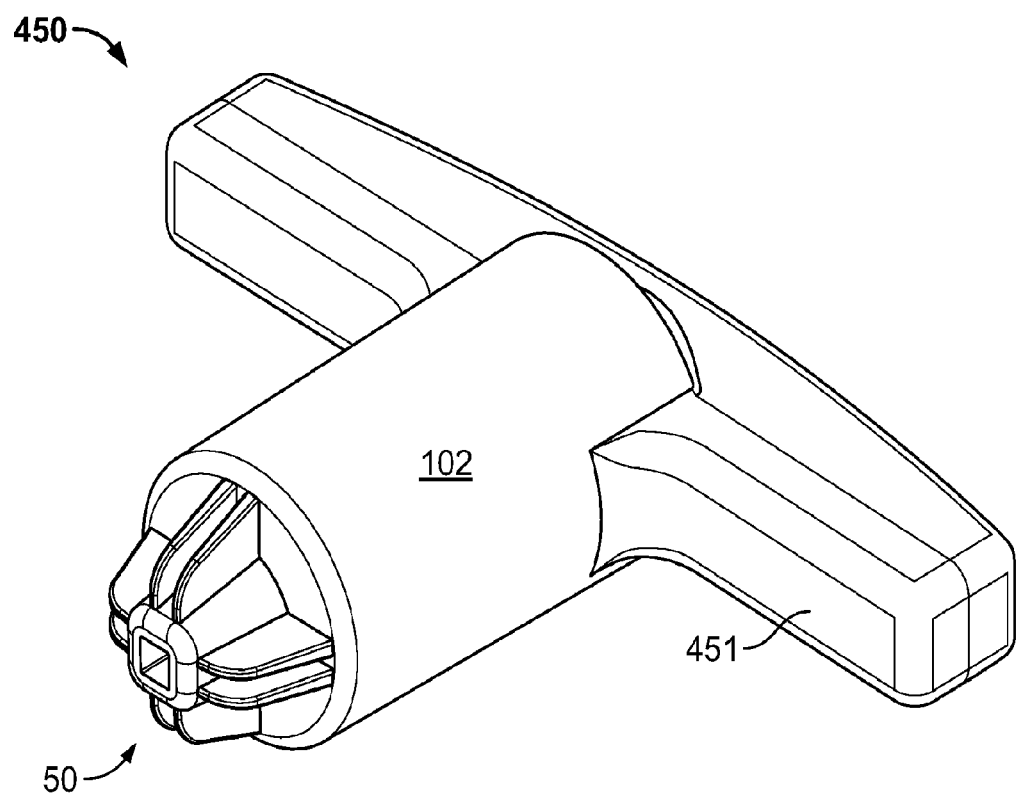
FIG. 11 is a fixed driver with a fortified mount.

According to one or more exemplary implementations, as shown in FIG. 11 illustrates a fix torque driver 450. Fixed torque driver 450 is shown with a generally T-shaped handle affixed to or formed as part of a cylindrical body 102. For example, the handle may by "T-shaped" however such a configuration is not a limitation. The handle may include arms 451. At an open end of the cylindrical body is affixed a plastic molded fortified connector mount "CM" 50 with a drive channel 150 at the end of the nose 100 molded to engage a shaft 400.

According to one or more exemplary implementations, when shaft 400 within said drive channel 150 is rotated at force one (F1) which is at the maximum tolerance of the fortified connector mount 50 the FBRs support the connection mount and prevent the wall structure of the nose 350 from distorting or breaking to failure under F1.

Figure 12:
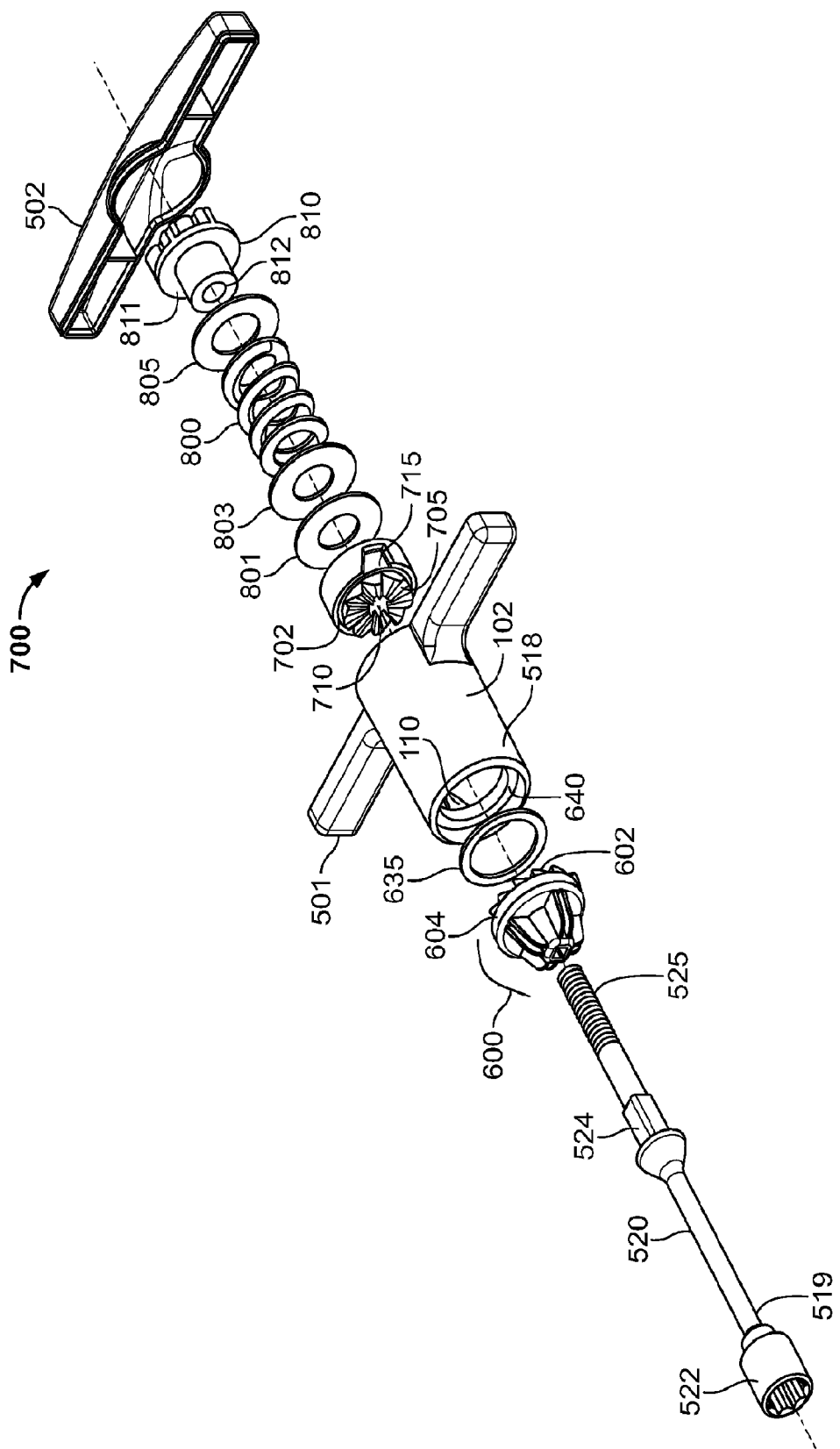
FIG. 12 is a torque limiting driver with a fortified mount.

According to one or more exemplary implementations, as shown in FIG. 12 illustrates a torque limiting driver 500 with a clutch mechanism and spring to limit the torque being applied to a predefined amount may be provided. Torque-limiting driver 500 is shown with a generally T-shaped handle or other structure to facilitate use by a user. For example, the handle may by "T-shaped" however such a configuration is not a limitation. The handle may include arms 501 at one end of an axially extending generally hollow cylindrical body 102. Cap 502 covers the same end of the handle. Cylindrical end 518 terminates cylindrical body 102 toward tip 519 of shaft 520. A toll such as a socket 522 or screw driver or hex mount or the like is affixed to or mount on the tip 519. Cap 502 may be snap-fitted to cylindrical body 108, or may be welded, adhered, or attached by any equivalent thereof.

An exemplary implementation shows, at least in part, at cylindrical end 518, lower shank 600 is provided, having a plastic molded fortified connector mount "CM" 50 at one end with a drive channel 150 at the end of the nose 100 molded to engage drive connection 524 of shaft 520. The CM 50 in this exemplary is formed as part of a circumferential rim 602 in place of the body. The circumferential rim is movable affixed within a body 102 whereby a gear system with springs provides a predetermined amount of torque during use.

An exemplary implementation shows, at least in part, shaft 520 provided, at one end, with tip 519, adapted for engagement with an associated tool 522 whereby a workpiece, such as a fastener or the like may be engaged. Workpiece engaging tool 522 is shown to be a socket wrench, but could be a screwdriver, wrench, or any other tool arrangement. At an opposite end, lower shank 600 has a plurality of teeth 602 arranged in a crown gear formation, with circumferential rim 604 extending radially outward and an internal axial bore to accommodate at least a portion of shaft 520 extending there through.

According to aspects of one or more exemplary implementations, inside cylindrical body 102 a clutch assembly is disposed. The clutch assembly includes an upper shank 700 for forcibly engaging lower shank 600. Upper shank 700 has a bottom face that has a plurality of teeth 702 arranged in a crown gear formation and upper shank rim 705 extending radially outward. Upper shank 700 includes annular outer shank wall 708 and axial bore 710 through the upper shank and running axially centered to the crown gear.

According to one or more exemplary implementations, upper shank 700 includes at least one recess 715 on a side of annular outer shank wall 708. Recess 715 is provided as a cylindrical cut, relief or recess into the side of the outer shank and maybe provided as a square or rectangular cut or the cut may have a slanted side or sides relative to the axis of upper shank 700. Not shown is a drive connection protruding from the interior annular wall 104 of the body 102, whereby the recess 715 is engaged, thereby rotating the upper shank, engaged with the lower shank and shaft and tip during use. The mechanism of action is such a device as described in applicant's pending PCT application, published as WO 2012/112591.

In assembly, drive connection 524 of shaft 520 is received into drive channel 150 of lower shank 600. Washer 635 maybe provided between inner shank rim 640 of lower shank 600 and circumferential flange 640 extending radially inward within the hollow of cylindrical body 102. Washer 635 may be of a polymer or other material having low coefficient of friction. Alternatively, inner shank rim 640 of lower shank 600 may be provided flush against circumferential flange 640. The opposite side of circumferential flange 640 receives upper shank rim 705 of upper shank 700, allowing teeth 602 of lower shank 600 to engage teeth 702 of upper shank 700 when a torque is applied.

According to aspects of one or more exemplary implementations, integrally formed within cylindrical body 102, protrusion 110 mates with recess 715 of upper shank 700. Protrusion 110 extends inward in a radial fashion and has a length along the axis of cylindrical body 102 for relative moveable engagement within recess 715. This engagement provides a locking mechanism of shaft 520 relative to the handle via upper shank 700 when pressure is applied across lower shank 600 and upper shank 700. Recess 715 is provided circumferentially wider than protrusion 110 for allowing cylindrical body 102 and the handle to rotate in reverse a predetermined distance from a locked position without subsequent reverse rotation of workpiece-engaging tool 522. Thus, at least one recess 715 and at least one protrusion 110 lock the handle in one direction providing the necessary torque to drive a fastener and allow for a predetermined amount of reverse rotation before unscrewing the fastener.

According to aspects of one or more exemplary implementations, force is applied across lower shank 600 and upper shank 700 via spring 800 within cylindrical body 102. Inside cylindrical body 102, washer one 801 and washer two 803 are provided between upper shank 700 and spring 800. Washer one 801 and washer two 803 transfer pressure from spring 800 over the top face of upper shank 700. At an end of spring 500 opposite upper shank 700, washer three 805 and shoulder nut 810 hold spring 800 in a relatively compressed state. Washer three 805 may be provided between nut 810 and spring 800 to facilitate relative rotation of nut 810 and spring 800. Nut 810 is formed of material softer than shaft 520. Nut 810 has an unobstructed open center 812 with a diameter smaller than the diameter of shaft 520 and a smooth surface malleable enough to be deformed by the rotational insertion to said open center 812 of the threading 525 at an end of shaft.

According to aspects of one or more exemplary implementations, various materials may be used for the components of driver 500. According to some exemplary implementations, at least one of body 102, nut 810, lower shank 600, and upper shank 700 and fortified connector mount "CM" 50 is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like, as well as blends or mixtures thereof. According to aspects of one or more exemplary implementations, at least one of lower shank 600 and upper shank 700 is of or includes at least one material that lubricous or otherwise reduces friction. The presence of a friction-reducing material allows geometric aspects of the engagement between lower shank 600 and upper shank 700 to govern whether teeth engage or disengage, thereby improving precision of the device.

According to aspects of one or more exemplary implementations, shaft 520 is of a rigid material. For example, shaft 520 may be of a metal, such as stainless steel. According to some exemplary implementations, high torque capabilities of driver 500 are, at least in part, provided by features that maintain an effective engagement between drive connection 524 of shaft 520 and drive channel 150 of lower shank 500. For example, some exemplary implementations are provided to improve the ability of driver 500 to maintain its grip on shaft 520 up to a greater range of torque.

This configuration enables greater torque capabilities than a piecemeal or fragmented set of interconnected components. This reduces the number of interconnections between a source of a torque and a location to which the torque is transferred.

According to one or more exemplary implementations, shaft 520 having drive connection 524 between opposing extensions stabilizes drive connection 524 within drive channel 150. Placement of drive connection 524 at a medial segment of shaft 520—rather than at an end thereof—facilitates a more stable engagement between drive connection 524 and drive channel 150, thereby increasing the ability of engagement to transfer high amounts of torque. When shaft 520 within said drive channel 150 is rotated at force one (F1) which is at the maximum tolerance of the fortified connector mount 50 the FBRs support the connection mount and prevent the wall structure of the nose 350 from distorting or breaking to failure under F1.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A plastic disposable driver (450) comprising:
   a connection mount (50) having:
   a nose (100) with a proximal end (128) formed as part of or affixed to a flat top (105) of a body (102);
   at least one pair of force buttressing ribs (120 & 120') extending from the flat top along the length of the nose;
   a distal end (125) of the connection mount;
   a square polygonal channel (150) guide having corners (155) the channel formed axial and centered in the nose of a size to accept a tool or shaft;
   wherein said force buttressing ribs each have a bottom (201) affixed at the flat top, each force buttressing rib has a support edge (210) affixed to the length of the annular wall (108) of the nose, each force buttressing ribs is formed around the annular wall in pairs positioned along one of the four sides of the square channel; and,
   a shaft (500) formed of a material harder than the polygonal channel mounted in said polygonal channel; and,
   wherein each force buttressing rib further comprises an interior edge (202) and an outer edge (200) wherein each member of the force buttressing rib pair is aligned with a corner of the square channel, and the outer edges of two adjacent pairs of force buttressing ribs align with the same corner of the square channel but at a 90 degree offset.

2. The driver of claim 1 further comprising one or more arms affixed to the body.

3. A fixed disposable driver comprising:
   a body (102) having an elongated nose (100) with a distal end (125) fluidly connected to an interior channel (150) formed axially therein;
   a wall (350) with a predetermined thickness surrounding the interior channel with an outer annular surface (108);
   a flat top (105) affixed to or formed as part of the proximal end (128) of the nose;
   at least one pair of force buttressing ribs (120 & 120') affixed to both the flat top and along the length of the outer annular surface; and,
   a shaft (500) formed of a material harder than the interior channel mounted in said channel;
   wherein the interior channel is square and has four corners (155);
   there are four pairs of force buttressing ribs each pair being parallel to each other and each pair aligned with one of the four walls of the interior channel; and
   each force buttressing rib further comprises an interior edge and an outer edge wherein each member of each force buttressing rib pair is aligned with a corner and the outer edges of two adjacent pairs of force buttressing ribs align with the same corner but at a 90 degree offset.

4. A plastic disposable torque limiting driver, comprising:
a connector mount (50) with a proximal end (128) formed as part of or affixed to a circumferential rim (602) and a distal end (125) comprising a nose (100);
at least two pairs of force buttressing ribs (120 & 120');
a square channel (150) guide having corners (155) the channel formed axial and centered in the nose of a size to accept a tool or shaft;
a shaft (500) formed of a material harder than the channel mounted in said square channel; and
wherein said force buttressing ribs have a bottom (201) affixed at the flat top and each force buttressing rib has a support edge (210) affixed to the nose;
wherein each force buttressing rib further comprises an interior edge and an outer edge wherein each member of the force buttressing rib pair is aligned with a corner and the outer edges of two adjacent pairs of force buttressing ribs align with the same corner but at a 90 degree offset.

5. A disposable torque-limiting driver comprising:
a handle (502) and an axially extending cylindrical body (102);
a torque-limiting assembly within the axially extending cylindrical body, the assembly comprising:
an upper cylindrical shank (700);
a lower cylindrical shank (600);
wherein the upper cylindrical shank and the lower cylindrical shank have a plurality of teeth (705) and an axial bore (710),
wherein the teeth spiral around the axial bore; and a spring (800) for applying pressure across the upper cylindrical shank and the lower cylindrical shank, wherein the teeth of the upper cylindrical shank and the lower cylindrical shank engage for relative rotation, and wherein the teeth disengage when a predetermined value of torque is exceeded; a locking screw threaded to mate with the lower cylindrical shank through the upper cylindrical shank;
a connector mount (50) with a nose (100) at its proximal end formed as part of the lower cylindrical shank;
four pairs of force buttressing ribs at the distal end of the nose;
a square channel (150) guide having corners (155) the channel formed axial and centered in the nose of a size to accept a tool or shaft;
wherein said force buttressing ribs each have a bottom (201) affixed at the flat top and each force buttressing rib has a support edge (210) affixed to the length of the nose each member of the force buttressing rib pair is aligned with a corner and the outer edges of two adjacent pairs of force buttressing ribs align with the same corner but at a 90 degree offset;
a shaft (500) formed of a material harder than the channel mounted in said channel; and,
a workpiece-engaging tip connected to the lower cylindrical shank.

6. A method of applying torque with a plastic disposable driver, the method comprising:
applying torque to a drive shaft (400), the shaft being affixed to a handle (102) via a square channel (150) having corners in a connector mount (50);
forming an annular wall (108) around the connector mount;
fortifying the connector mount with four pairs of force buttressing ribs (120 & 120') whereby load from the shaft excreting force on the annular wall is transferred to a flat top (105) of the connector mount; and,
whereby the connection mount is further strengthened by positioning two force buttressing ribs 90 degrees apart at each same corner and operates without failure at a load between a force (F1) of 85 and 115 pound-feet for a predetermined time.

7. The method of claim 6, wherein the predetermined time is at least 8 seconds.

8. The method of claim 6, wherein the predetermined time is at least 9 seconds.

9. The method of claim 6, wherein the predetermined time is at least 10 seconds.

10. The method of claim 6, whereby the connection mount holds the shaft without failure at a load between a force (F1) of 140 and 150 pound-feet for at least 10 seconds.

11. The method of claim 6, whereby the connection mount holds the shaft without failure at a load between 140 and 150 pound-feet for at least 12 seconds.

12. The method of claim 6, whereby the connection mount holds the shaft without failure at a load between 140 and 150 pound-feet for at least 15 seconds.

13. The method of claim 6, whereby the connection mount holds the shaft without failure at a load between 140 and 150 pound-feet for at least 16 seconds.

14. The method of claim 6, whereby the connection mount holds the shaft without failure at a load between 140 and 150 pound-feet for at least 17 seconds.

15. The method of any one of claim 6, wherein a non-fortified mount will at least one of distort, deform, and break the annular wall (108) during the predetermined time in the absence of the strategically placed force buttressing ribs when the force (F1) is applied.

* * * * *